(12) United States Patent
Olsen

(10) Patent No.: US 8,298,593 B2
(45) Date of Patent: Oct. 30, 2012

(54) NUTRITIONAL SUPPLEMENT FOR USE WITH POULTRY AND LIVESTOCK

(75) Inventor: Randy H. Olsen, St. Cloud, MN (US)

(73) Assignee: JRW Technologies, LLC, Willmar, MN (US)

( * ) Notice: Subject to any disclaimer, the term of this patent is extended or adjusted under 35 U.S.C. 154(b) by 206 days.

(21) Appl. No.: 12/660,722

(22) Filed: Mar. 3, 2010

(65) Prior Publication Data

US 2011/0027387 A1  Feb. 3, 2011

(51) Int. Cl.
*A61K 36/00* (2006.01)
*A61K 36/45* (2006.01)

(52) U.S. Cl. ........ 424/732; 424/725; 424/773; 424/774; 424/775; 424/776; 424/777; 424/778; 424/779

(58) Field of Classification Search .................. 424/725, 424/732, 773–779
See application file for complete search history.

(56) References Cited

U.S. PATENT DOCUMENTS

| 5,518,750 | A |   | 5/1996  | Meneff ................... 426/507 |
| 5,863,775 | A |   | 1/1999  | Atkinson et al. ........... 435/172.3 |
| 5,997,911 | A |   | 12/1999 | Brinton et al. ............. 424/632 |
| 6,156,355 | A | * | 12/2000 | Shields et al. ............. 426/74 |
| 7,153,504 | B2|   | 12/2006 | Follette et al. ........... 424/94.21 |
| 7,258,879 | B1|   | 8/2007  | Hodge et al. .............. 426/2 |
| 7,416,742 | B2|   | 8/2008  | McNeff et al. ............. 424/662 |
| 7,485,325 | B2|   | 2/2009  | Swain .................... 424/738 |
| 2006/0024405 | A1 |   | 2/2006  | Warf, Jr. et al. ........... 426/2 |
| 2007/0085059 | A1 |   | 4/2007  | Mora-Gutierrez et al. .......... 252/400.21 |
| 2008/0260892 | A1 |   | 10/2008 | Fisher .................... 426/2 |

FOREIGN PATENT DOCUMENTS

WO    WO 2007/106473 A2  *  9/2007

OTHER PUBLICATIONS

Li et al. "Identification of Antioxidants in Essential Oil of Radix Angelicae Sinensis Using HPLC Coupled with DAD-MS and ABTS-Based Assay," J. Agric. Food Chem. 2007, 55, pp. 3358-3362.*
Sacchetti et al. "Comparative evaluation of 11 essential oils of different origin as functional antioxidants, antiradicals, and antimicrobials in foods," Food Chemistry 2005, 91, pp. 621-632.*
List of essential oils, accessed on Feb. 13, 2012 at en.wikipeida.org/wiki/List_of_essential_oils.*
"Essential Oil" accessed at en.wikipedia.org/wiki/Essential_oil on Feb. 13, 2011.*

* cited by examiner

*Primary Examiner* — James H. Alstrum-Acevedo
(74) *Attorney, Agent, or Firm* — Richard C. Emery

(57) ABSTRACT

A first composition including copper sulfate, citric acid, ammonium carbonate, propionic acid, *Yucca schidigera* extract, and antioxidants from essential oils and a second composition including sodium acid sulfate, citric acid and antioxidants from essential oils are sequentially administered to livestock through the drinking water supply to reduce the incidence of diseases such as *Clostridium*, *E. coli* and *Salmonella* and, thus, reliance on antibiotics to control the diseases.

11 Claims, 6 Drawing Sheets

NUTRITIONAL SUPPLEMENT FOR USE WITH POULTRY AND LIVESTOCK

FIELD OF THE INVENTION

The invention relates to nutritional feed supplements added to the drinking water of domesticated livestock and poultry.

BACKGROUND

Domesticated livestock such as cattle, swine, chickens, turkeys and other livestock are frequently raised in confinement growing facilities that are environmentally controlled. While environmentally controlled, poultry and livestock raised under such intense growing conditions can nevertheless lead to stress for the animals. Overcrowding can engender unhealthy living conditions for the subject animals by increased exposure to various types of microorganisms. When living microorganisms such as bacteria, viruses, *rickettsia*, fungi and protozoans enter the body and multiply, they cause a disturbance of normal bodily function and disease can occur. Diseased animals lead to losses for the producer for many reasons: (1) death of the animal; (2) medication costs; (3) condemnations at the processing plant; (4) poor growth; (5) poor production; (6) poor feed conversion; and (7) downgrading of agricultural product. Disease is caused by chemical toxins produced by the invading organisms. Diseases such as *Clostridium, E. coli* and *Salmonella* are often managed by exposure to antibiotics which are usually administered to the livestock with the feed and/or drinking water. While antibiotics can be an effective treatment to bacterial diseases among livestock, problems can also result from antibiotic use: (1) Antibiotic resistance can develop among certain bacterial strains, often due to overuse of antibiotics; (2) Antibiotics are a relatively expensive treatment, which necessitates raising the cost of the finished agricultural product; and (3) Some antimicrobial strains emerging in livestock can be transmitted to humans, through meat and other animal derived foods or through direct contact with livestock. What is clearly needed, then, is an improved treatment for diseases in livestock to reduce dependence on antibiotics.

SUMMARY

In one embodiment the invention comprises a first composition for improving the quality and quantity of production in poultry by reducing the incidence of necrotic enteritis, including, in combination, copper sulfate, citric acid, ammonium carbonate, propionic acid, *Yucca schidigera* extract, and antioxidants from essential oils.

In another embodiment, the invention comprises a second composition for improving the quality and quantity of production in poultry by reducing the incidence of necrotic enteritis, including, in combination, sodium acid sulfate, citric acid and antioxidants from essential oils.

In yet another embodiment, the invention comprises a method of administering nutritional supplements to poultry, comprising the steps of: in a first phase, administering feed and water to the chicks for a period of several days; in a second phase, following the first phase, administering to the chicks feed, water and a first composition comprising water, copper sulfate, citric acid, ammonium carbonate, propionic acid, *Yucca schidigera* extract, and antioxidants from essential oils for a period of several days; in a third phase, following the second phase, administering feed and water to the chicks for a period of several days following the second phase; in a fourth phase, following the third phase, administering to the chicks feed, water and a second composition comprising sodium acid sulfate, citric acid and antioxidants from essential oils for a period of several days; and in a fifth phase, following the fourth phase, administering feed, water and the first composition to the chicks for a period of approximately three days a week until the chicks are harvested.

In a further embodiment, the invention comprises a method of administering nutritional supplements to poultry, comprising the steps of: in a first phase, administering feed and water to the chicks for a period of approximately 5 days following the hatch of the chicks; in a second phase, administering to the approximately 5 day old chicks feed, water and a first composition comprising water, copper sulfate, citric acid, ammonium carbonate, propionic acid, *Yucca schidigera* extract, and antioxidants from essential oils for a period of 10 days; in a third phase, administering feed and water to the approximately 15 day old chicks for a period of 5 days until the chicks are approximately 20 days old; in a fourth phase, administering to the approximately 20 day old chicks feed, water and a second composition comprising sodium acid sulfate, citric acid and antioxidants from essential oils for a period of 5 days until the chicks are approximately 25 days old; in a fifth phase, administering feed, water and the first composition to the approximately 25 day old chicks for a period of approximately 3 days a week until the chicks are harvested.

DETAILED DESCRIPTION

Definitions

Figure 1:
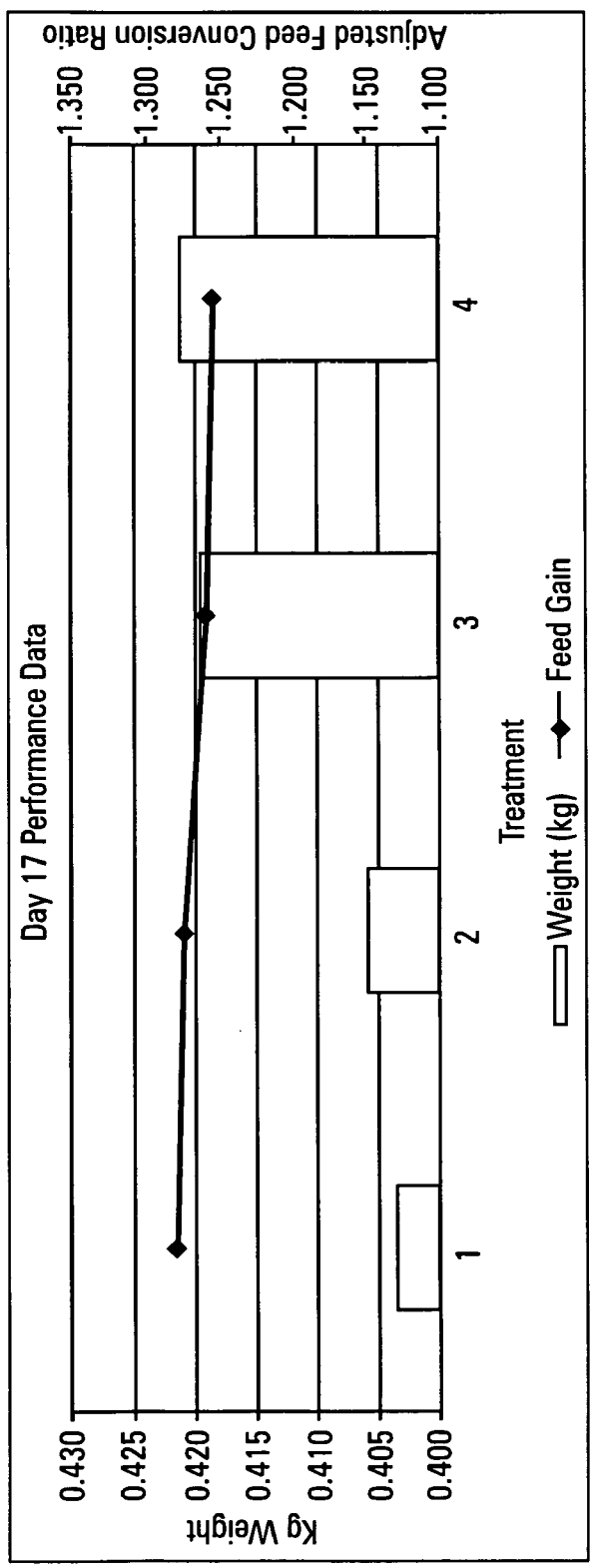
FIG. 1 is a graph illustrating test results at day 17 following administration of Composition I after day 5, showing average weight in kilograms and adjusted feed conversion.

"Broiler" means a chicken breed raised specifically for meat production. Modern commercial broilers are typically known as Cornish crosses or Cornish-Rocks and are specially bred for large scale, efficient meat production and grow much faster than egg or traditional dual-purpose breeds.

"Chick" is used generically herein to mean the young of any kind of poultry.

"Cranberry Water" means the first step pressing from the cranberry crushing process, wherein the juice pressed from harvested cranberries is not concentrated or rendered down.

"Disease" means an alteration of the body or body organs which interrupt or disturb the body's normal functioning.

"Feed Conversion Ratio" means a measure of an animal's efficiency in converting feed mass into increased body mass. More specifically, the mass of the food eaten is divided by the body mass gain, over a specific period. A lower feed conversion ratio indicates a lesser amount of feed is required to produce a higher weight of meat. A lower feed conversion ratio is therefore desirable.

"Poultry" means domesticated birds raised for their eggs, meat, leather or feathers. Examples include but are not limited to chickens, domesticated ducks, emu, geese, Indian peafowl, Mute swan, ostrich, turkeys, domesticated guineafowl, common pheasant, golden pheasant and rhea.

"Supplement" means Composition I and/or Composition II.

The present invention comprises compositions that can be added to the drinking water and/or feed of commercially raised livestock and poultry to greatly enhance the animals' natural ability to resist disease, thereby reducing the need for additional antibiotics. The composition may be in a liquid form to be combined with the animals' drinking water or it may be a powder able to be mixed with feed or dissolved or dispersed in a liquid carrier.

Composition (Composition I)

In a first composition, the invention comprises a mixture of water, copper sulfate, citric acid, ammonium carbonate, propionic acid, *Yucca schidigera* extract, and antioxidants from essential oils. In one embodiment, the antioxidants from essential oils comprise cranberry water, which is an aqueous extract produced from mechanically pressing the cranberry fruit, *Vaccinium macrocarpon* and/or the cranberry fruit seed as the first step of processing cranberries before any rendering down or concentration takes place. One embodiment of the additive uses a proportion of approximately 720 gallons water, approximately 1800 pounds plus or minus 500 pounds of copper sulfate, approximately 1355 pounds citric acid plus or minus 500 pounds, approximately 180 lbs ammonium carbonate, approximately 452 pounds propionic acid plus or minus 100 pounds, approximately 30 gallons *Yucca schidigera* extract plus or minus 10 gallons added to approximately 64 gallons plus or minus 32 gallons of cranberry water. In another embodiment, a red dye such as sodium benzoate may be added to Composition I. In an alternative embodiment an anti-foam agent such as propylene glycol may be added to Composition I to reduce foaming during addition to the drinking water supply. While it is known that this particular blend of ingredients is safe and effective in enhancing the immune system of poultry receiving it in its drinking water, it is believed that other proportions would also work, thus, the invention is not so limited and also contemplates other proportions of copper sulfate, citric acid, ammonium carbonate, propionic acid, *Yucca schidigera* extract and antioxidants from different essential oils. It is known that other livestock types (cattle, swine and others) require different proportions due to greatly differing body weight, species, living conditions and physiology, thus, the invention also contemplates and is therefore within the scope of the use of a differently proportioned mixture with such animals.

The following table reflects the percent by weight of the ingredients of Composition I.

Composition I

TABLE 1

| Ingredient | Weight Added (lbs) | | | Weight Percent | | |
| --- | --- | --- | --- | --- | --- | --- |
| | Max | Target | Min | Max | Target | Min |
| Water | 6008 | 6008 | 6008 | 49.9% | 56.7% | 65.7% |
| Copper sulfate | 2300 | 1800 | 1300 | 19.1% | 17.0% | 14.2% |
| Citric Acid | 1855 | 1355 | 855 | 15.4% | 12.8% | 9.4% |
| Ammonium Carbonate | 180 | 180 | 180 | 1.5% | 1.7% | 2.0% |
| Propionic Acid | 552 | 452 | 352 | 4.6% | 4.3% | 3.8% |
| *Yucca schidigera* extract | 334 | 250 | 166 | 3.1% | 2.6% | 2.0% |
| Antioxidants from Essential Oils | 801 | 534 | 267 | 6.6% | 5.0% | 2.9% |
| Total | 12030 | 10579 | 9128 | 100.0% | 100.0% | 100.0% |

Manufacture (Composition I)

Combining the water, copper sulfate, citric acid, ammonium carbonate, propionic acid, *Yucca schidigera* extract and antioxidants from different essential oils (cranberry water in one embodiment) is accomplished by adding the dry ingredients (ammonium carbonate, copper sulfate, citric acid and propionic acid) in that order to the liquid ingredients (water, *Yucca schidigera* extract, cranberry water) while stirring the water, *Yucca schidigera* extract and cranberry water at a temperature of approximately 90-100 degrees F. for a period of approximately two hours. There is an approximate five minute interval between the addition of each dry ingredient. The stirring action results in the solid ingredients becoming dissolved into the liquid ingredients (water, *Yucca schidigera* extract, cranberry water) leading to the finished supplement. Following successful mixing, Composition I is then bottled and shipped to distributors for eventual distribution to end users.

To prepare in one embodiment Composition I for use, approximately 128 liquid ounces of the supplement is added to approximately 512 gallons of water, which is then consumed by the poultry or livestock as described below. In another embodiment, approximately 128 liquid ounces of Composition I can be added to a range of between approximately 512 to 1,024 gallons of water.

Composition (Composition II)

In a second composition, the invention comprises a mixture of sodium acid sulfate (SAS), citric acid and antioxidants from essential oils. In one sub-embodiment, the antioxidants from essential oils comprises cranberry water, which is an aqueous extract produced from mechanically pressing the cranberry fruit, *Vaccinium macrocarpon* and/or the cranberry fruit seed as the first step of processing cranberries before any rendering down or concentration takes place. One embodiment of the composition uses a proportion of approximately 250 pounds plus or minus 150 pounds of sodium acid sulfate, approximately 250 pounds citric acid plus or minus 150 pounds of with approximately 1000 gallons of cranberry water. While it is known that this particular blend of ingredients is safe and effective in enhancing the immune system of poultry receiving it in its drinking water it is believed that other proportions would also work, thus, the invention is not so limited and further contemplates other proportions of sodium acid sulfate, citric acid and antioxidants from different essential oils. It is known that other livestock types (cattle, swine and others) require different proportions due to greatly differing body weight, species, living conditions and physiology, thus, the invention also contemplates and is therefore within the scope of the use of a differently proportioned mixture with such animals.

The following table reflects the percent by weight of the ingredients of Composition II.

Composition II

TABLE 2

| Ingredient | Weight Added (lbs) | | | Weight Percent | | |
|---|---|---|---|---|---|---|
| | Max | Target | Min | Max | Target | Min |
| Citric Acid | 400 | 250 | 100 | 4.4% | 2.9% | 1.2% |
| Antioxidants from Essential Oils | 8345 | 8345 | 8345 | 91.2% | 94.3% | 97.6% |
| Sodium Acid Sulfate | 400 | 250 | 100 | 4.4% | 2.9% | 1.2% |
| Total | 9145 | 8845 | 8545 | 100% | 100% | 100% |

Manufacture (Composition II)

Prior to mixing, the cranberry water is maintained at a temperature of approximately 40 degrees F., while the dry ingredients (sodium acid sulfate and citric acid) are kept at room temperature. Approximately 43 pounds of sodium acid sulfate (SAS) and 43 pounds of citric acid are added to approximately 165 gallons of cranberry water. The ingredients are mixed until the sodium acid sulfate and citric acid are completely dissolved into the cranberry. Following successful mixing, Composition II is then bottled and packaged for shipping.

To prepare in one embodiment Composition II for use, approximately 20 to 40 liquid ounces of Composition II are added to approximately 512 gallons of water.

Method of Use

Composition I and Composition II are administered to the livestock through its drinking water which is typically provided to poultry and other livestock through an automated watering system. In a first phase, following hatch, for a period of approximately 5 days, the chicks receive feed and water. In a second phase, broilers (chickens specifically bred and raised for their meat) receive feed, water and Composition I at around 5 days following hatch for a period of approximately 10 days, to the age of approximately 15 days. In a third phase, following the initial administration of Composition I, the broiler chicks again receive feed and water for a period of about 5 days, until the age of about 20 days. In a fourth phase, at around 20 days age the broiler chicks are administered feed, water and Composition II for a period of about 5 days until the age of about 25 days. Finally, in a fifth phase, the broiler chicks are again administered feed, water and Composition I for about 2-3 days a week until harvest. The harvest period varies between 40 and 63 days depending on the final animal size desired by the producer.

Testing Procedure

The test facility was divided into ten blocks of four pens. Treatments were assigned to the pens using a complete randomized block design. Broiler chicks were assigned to the pens randomly. Specific treatment groups were as follows:

| Treatment | Clostridia Challenge | Test Article | No. of Birds/Pen* | No. of Pens | No. of Birds/Treatment |
|---|---|---|---|---|---|
| 1 | No | Negative Control | 28 | 10 | 280 |
| 2 | Yes | Negative Control | 28 | 10 | 280 |
| 3 | No | Composition I/Composition II | 28 | 10 | 280 |
| 4 | Yes | Composition I/Composition II | 28 | 10 | 280 |
| | | Totals | | 40 | 1,120 |

*28 birds were placed in pens on day 0, on day 7 the birds were recounted and the number of birds per pen was adjusted to 26.

Treatments 1 and 2 received no Composition I or Composition II in the drinking water supplies. Composition I was added to the chicks' drinking water supply in treatments 3 and 4 from days 5-15, 25-28 and 31-34. Composition II was added to the chicks' drinking water supply in treatments 3 and 4 on days 16-22 and days 38 to study end.

Water treatments were provided to each pen using a 5 gallon bucket attached to an automated bell drinker. 69.3 ml of Composition II was mixed with 30 gallons of water resulting in a 1:1638 gallon dilution. 222 ml of Composition I was added to 30 gallons of water resulting in a 1:512 gallon dilution.

Results

After water, the largest component of Composition I is copper sulfate, which is readily soluble in water, completely ionizing to $Cu^{2+}$ and $SO_4^{2-}$. The next largest component is citric acid, which is a propionic acid with 3 ionizable hydrogen atoms, the first with a pKa of 3.1, the second with a pKa of 4.8 and the third with a pKa of 6.4. Similarly the propionic acid has a pKa of 4.9. The ammonium carbonate is used in small amounts and would neutralize only a modest amount of the acid. The antifoam agent is a nonreactive component and the red dye is added in such small amounts as not likely to be a factor. Overall, the effect of these ionic ingredients is to create an acidic solution balanced with large quantities of basic ions, specifically the sulfate ($SO_4^{2-}$) and the citrate.

The extract of cranberries includes phenolics, a broad class of chemical compounds based on reactions of phenols and other chemicals found within the plant. It has been found that cranberry extracts are effective against *Clostridium*. Similarly, it is known that extracts of *Yucca* plants are high in saponins, a class of chemicals that are effective against certain *Clostridium* species. It is also known that *Yucca* extracts improve digestive tract health by acidification.

It is possible that individually the acidic nature of the solution, the cranberry phenols and the *Yucca* saponins can contribute to the efficacy of Composition I. It is further believed that the combination leads to a synergistic effect as illustrated in FIGS. 1-4.

FIG. 1 is a graph illustrating test results at day 17 following administration of Composition I after day 5, showing average weight in kilograms and adjusted feed conversion via the vertical bars. It is seen that in Treatment 1, which is a negative control where no treatment of Composition I has been provided and no exposure to *Clostridium* that the average bird weight is 0.403 kilograms. Treatment 2 is also a negative control where no treatment of Composition I has been provided but the birds have been exposed to *Clostridium* that the average bird weight is only slightly higher at 0.406 kilograms. Treatment 3 illustrates the scenario where the birds received Composition I between days 6-15 and no exposure to *Clostridium*. It is seen that the average bird weight improves to 0.419. Treatment 4 illustrates the scenario where the birds received Composition I between days 6-15 and are exposed to *Clostridium* the average weight increases to 0.421.

FIG. 1 also illustrates the effect of administration of Composition I on Feed Conversion Ratio (FCR), which is shown by the horizontally oriented line. In Treatment 1 the FCR is 1.279, Treatment 2 is 1.273, Treatment 3 is 1.256 and Treatment 4 is 1.252.

Figure 2:
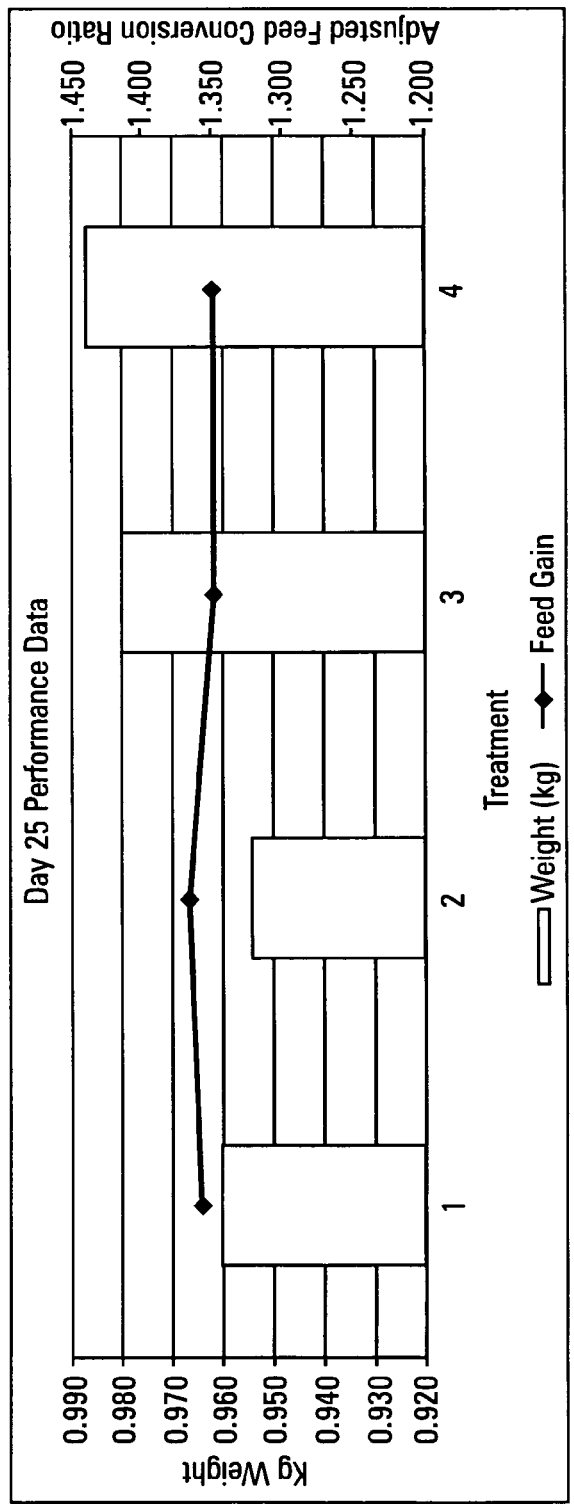
FIG. 2 is a graph illustrating test results at day 25 following administration of Composition II after day 21, showing average weight and adjusted feed conversion.

FIG. 2 is a graph illustrating test results at day 25 following administration of Composition II between days 21-25, showing average weight and adjusted feed conversion. It is seen that in Treatment 1, which is a negative control where no treatment of Composition I has been provided and no exposure to *Clostridium* that the average bird weight is 0.961 kilograms. Treatment 2 is also a negative control where no treatment of Composition I has been provided but the birds have been exposed to *Clostridium* that the average bird weight is only slightly higher at 0.954 kilograms. Treatment 3 illustrates the scenario where the birds received Composition I between days 6-15 and no exposure to *Clostridium*. It is seen that the average bird weight improves to 0.980 kilograms. Treatment 4 illustrates the scenario where the birds received Composition I between days 6-15 and are exposed to *Clostridium*, the average weight increases to 0.987 kilograms.

FIG. 2 also illustrates the effect of administration of Composition II on Feed Conversion Ratio (FCR), which is shown by the horizontally oriented line. In Treatment 1 the FCR is 1.360, Treatment 2 is 1.368, Treatment 3 is 1.349 and Treatment 4 is 1.350.

Figure 3:
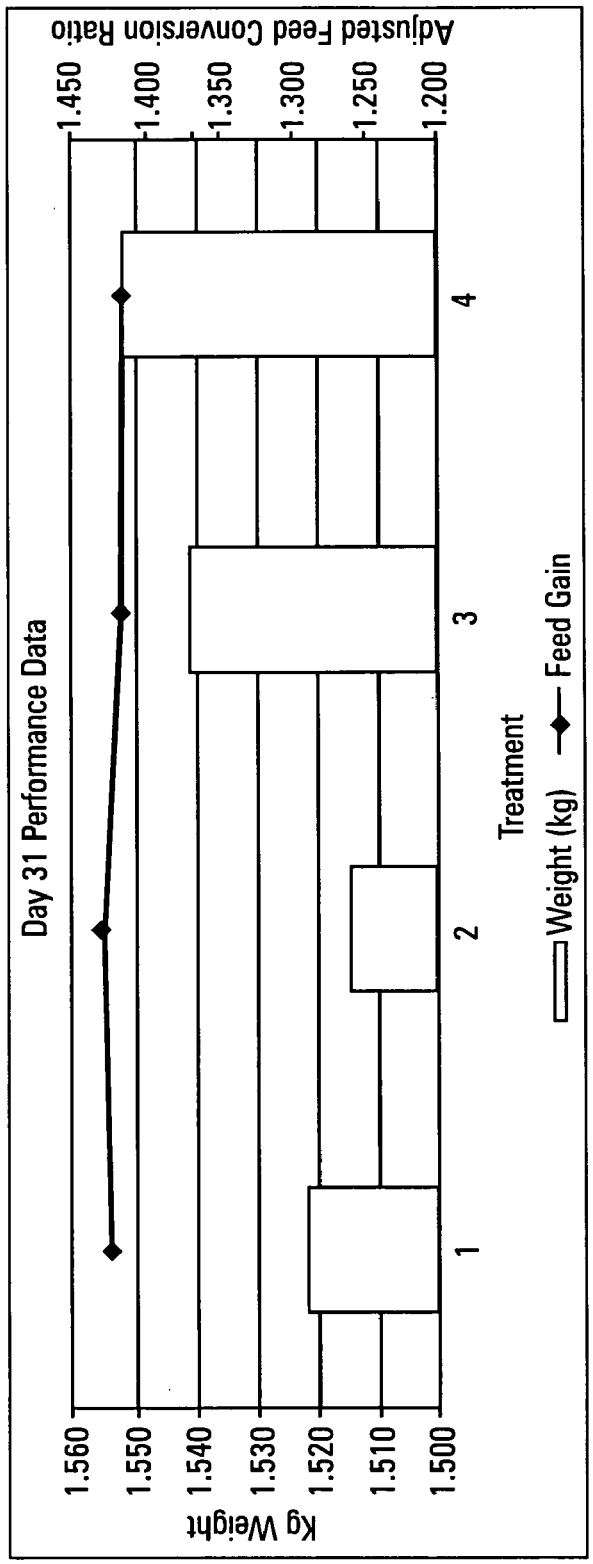
FIG. 3 is a graph illustrating test results at day 31 following administration of Composition I 2-3 times a week, showing average weight and adjusted feed conversion.

FIG. 3 is a graph illustrating test results at day 31 following administration of Composition I 2-3 times a week, showing average weight and adjusted feed conversion. It is seen that in Treatment 1, which is a negative control where no treatment of Composition I has been provided and no exposure to *Clostridium* that the average bird weight is 1.522 kilograms. Treatment 2 is also a negative control where no treatment of Composition I has been provided but the birds have been exposed to *Clostridium* that the average bird weight is only slightly higher at 1.514 kilograms. Treatment 3 illustrates the scenario where the birds received Composition I between days 6-15 and no exposure to *Clostridium*. It is seen that the average bird weight increases to 1.541. Treatment 4 illustrates the scenario where the birds received Composition I between days 6-15 and are exposed to *Clostridium* the average weight increases to 1.552.

FIG. 3 also illustrates the effect of administration of Composition I on Feed Conversion Ratio (FCR), which is shown by the horizontally oriented line. In Treatment 1 the FCR is 1.423, Treatment 2 is 1.429, Treatment 3 is 1.414 and Treatment 4 is 1.413.

Figure 4:
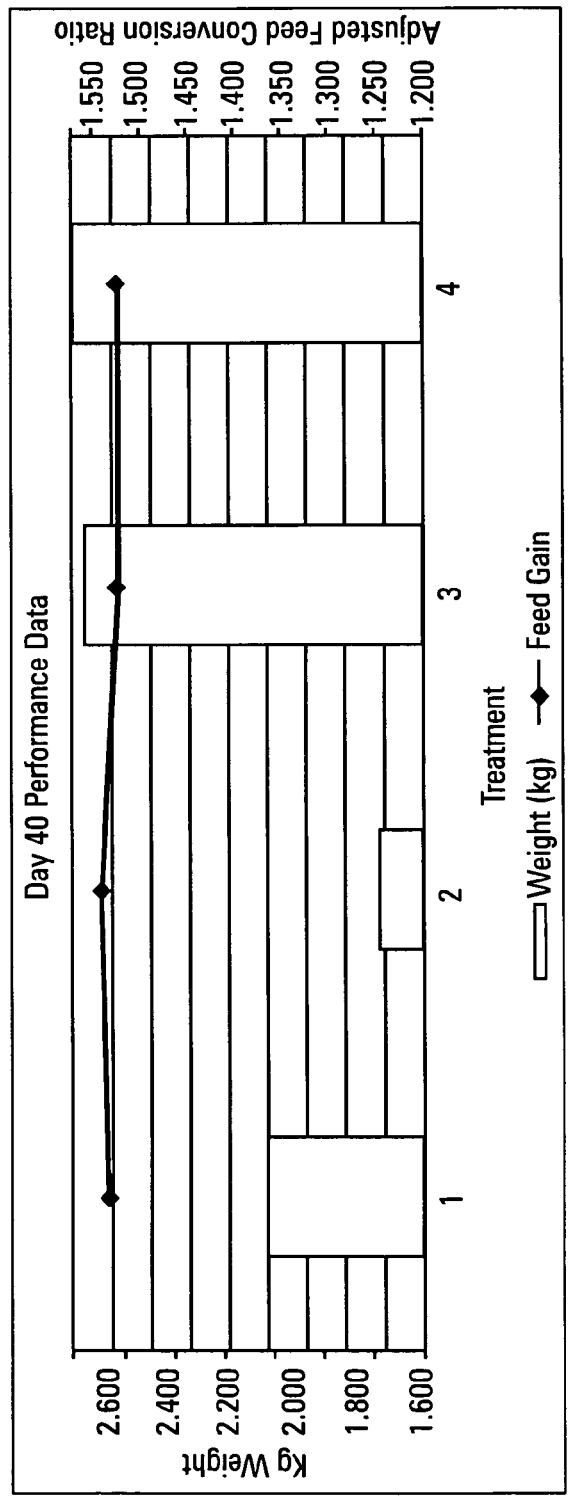
FIG. 4 is a graph illustrating test results at day 40 following administration of Composition I 2-3 times a week after day 31, showing average weight and adjusted feed conversion.

FIG. 4 is a graph illustrating test results at day 40 following administration of Composition I 2-3 times a week after day 31, showing average weight and adjusted feed conversion. It is seen that in Treatment 1, which is a negative control where no treatment of Composition I has been provided and no exposure to *Clostridium* that the average bird weight is 2.490 kilograms. Treatment 2 is also a negative control where no treatment of Composition I has been provided but the birds have been exposed to *Clostridium* that the average bird weight is lower at 2.461 kilograms. Treatment 3 illustrates the scenario where the birds received Composition I between days 6-15 and no exposure to *Clostridium*. It is seen that the average bird weight improves to 2.537. Treatment 4 illustrates the scenario where the birds received Composition I between days 6-15 and are exposed to *Clostridium* the average weight increases to 2.539.

FIG. 4 also illustrates the effect of administration of Composition I on Feed Conversion Ratio (FCR), which is shown by the horizontally oriented line. In Treatment 1 the FCR is 1.533, Treatment 2 is 1.540, Treatment 3 is 1.521 and Treatment 4 is 1.522.

Figure 5:
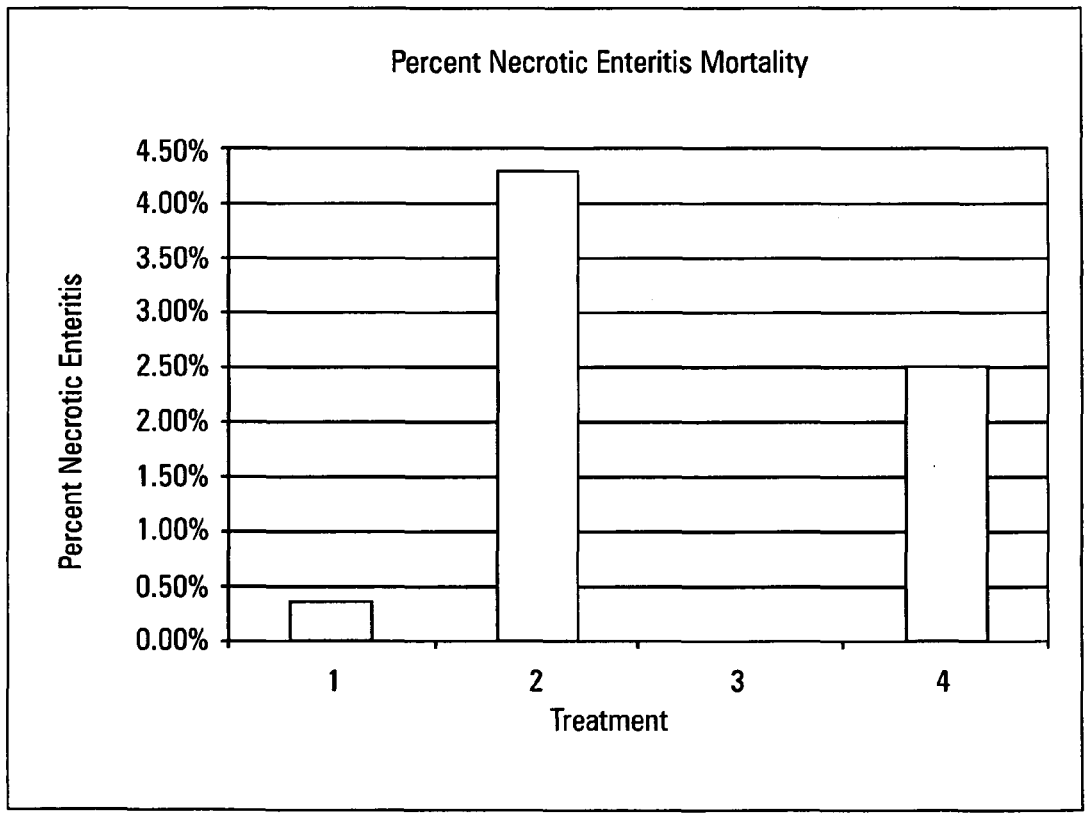
FIG. 5 is a graph illustrating percent Necrotic Enteritis Mortality following completion of the study.

FIG. 5 is a graph illustrating percent Necrotic Enteritis Mortality following completion of the study. It is seen that in Treatment 1, which represents an unchallenged (*Clostridium*) negative control (no supplements introduced), the percent of necrotic enteritis mortality is extremely low, approximately 0.36 percent. In Treatment 2, which represents a *Clostridium* challenged population treated with the supplements, it is noted that necrotic enteritis mortality is dramatically higher, at 4.29 percent. Treatment 3 resulted in no necrotic enteritis mortality, where the population was unchallenged by *Clostridium* and the supplements were introduced. Finally, in Treatment 4 where the population was challenged by *Clostridium* and the supplements were introduced, it is noted that necrotic enteritis mortality is reduced almost in half from Treatment 2, at 2.5 percent.

Figure 6:
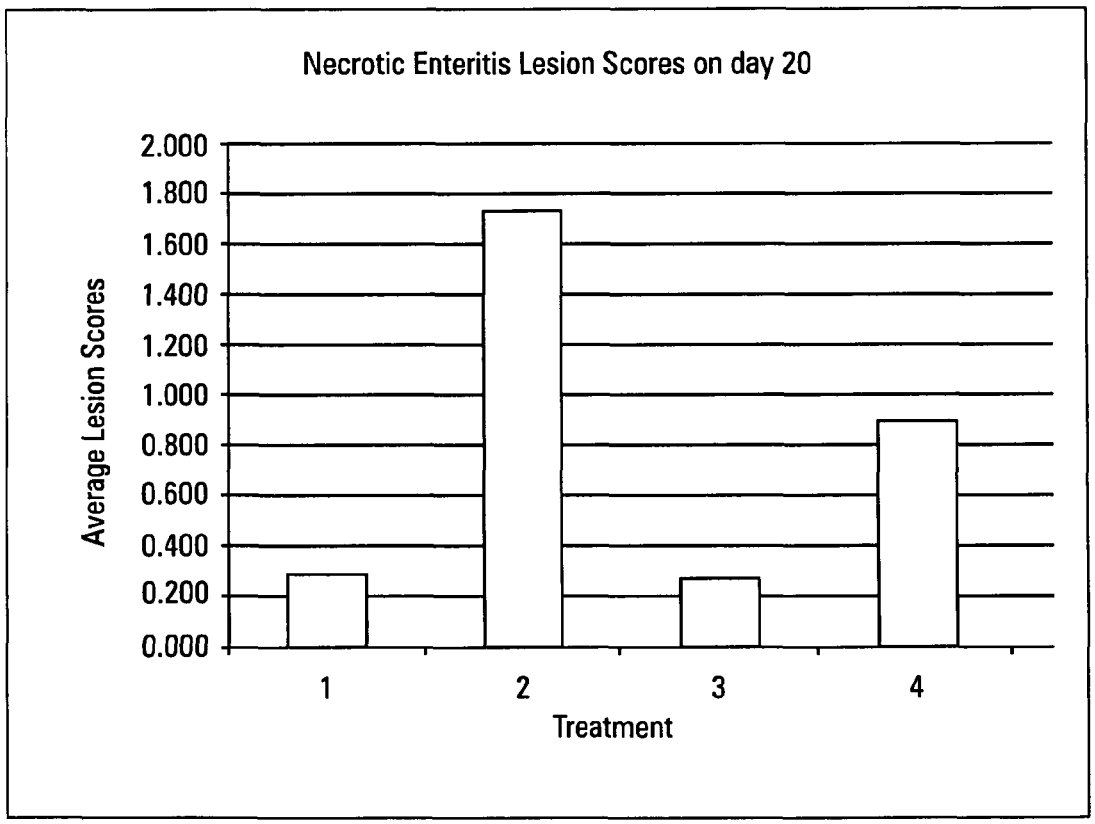
FIG. 6 is a graph illustrating Necrotic Enteritis Lesion Scores on day 20.

FIG. 6 is a graph illustrating Necrotic Enteritis Lesion Scores on day 20. It is seen that in Treatment 1, which represents an unchallenged (Clostridium) negative control (no supplements introduced), the necrotic enteritis lesion score is low, 0.30. In Treatment 2, which represents a *Clostridium* challenged population treated with the supplements, it is noted that the necrotic enteritis lesion score is dramatically higher, at 1.74. Treatment 3, where the population was unchallenged by *Clostridium* and the supplements were introduced, resulted in a lowered necrotic enteritis lesion score at 0.28. Finally, in Treatment 4 where the population was challenged by *Clostridium* and the supplements were introduced, it is noted that the necrotic enteritis lesion score is reduced almost in half from Treatment 2, at 0.9.

In Composition I it is possible that there are reactions between the basic ions ($Cu^{2+}$, $SO_4^{2-}$ and the citrate) leading to an improved pharmaceutical nature of the phenols and saponins, most likely the water solubility. Additionally, it is possible that salts of basic counterions are formed with the phenols and saponins, leading to improved performance.

Using Composition I and Composition II in combination as described above provides demonstrable advantages to poultry and other livestock producers. As an example, for Broilers at 42 days of age, the Return on Investment is dramatic:

Total Amount of Composition I used: 34 gallons × $18.75 = $637.50

Total Amount of Composition II used: 4 gallons × $45.00 = $180.00

Cost $817.50

Weight gain improvement of 0.2 lbs/bird×25,000×a market of $00.58/lb=$2,900.

3 points improvement in Feed Conversion Ratio (assuming $200.00/ton feed cost)

25,000×5.5858 lb weight=139,645 lbs of live weight 139,645×0.03=4,189 lbs. of feed saved=@ 2.0946 ton× 200=$418.94

Total savings=$3,318.94/25,000 broilers

This equals a 4:1 return on investment ($3,318.94/$817.50=4.05)

What is claimed is:

1. A composition for improving the quality and quantity of production in poultry by reducing the incidence of necrotic enteritis, the composition comprising:

a. water;
b. copper sulfate;
c. citric acid;
d. ammonium carbonate;
e. propionic acid;
f. *Yucca schidigera* extract; and
g. cranberry water.

2. The composition of claim 1 further comprising propylene glycol.

3. The composition of claim 1 further comprising sodium benzoate.

4. The composition of claim 1 having proportions comprising 720 gallons of the water, a range of the copper sulfate of between approximately 1300 to 2300 pounds, a range of the citric acid of between approximately 855 to 1855 pounds, the ammonium carbonate of approximately 180 pounds, a range of the propionic acid of between approximately 352 to 552 pounds, between approximately 20 to 40 gallons of the *Yucca schidigera* and between approximately 32 to 96 gallons of the cranberry water.

5. The composition of claim 4 wherein to approximately 720 gallons of the water the copper sulfate is present at a proportion of approximately 1800 pounds, the citric acid is present at a proportion of approximately 1355 pounds, the ammonium carbonate is present at a proportion of approximately 180 pounds and the propionic acid is present at a proportion of approximately 452 pounds, the *Yucca schidigera* is present at a proportion of approximately 30 gallons and the cranberry water is present at a proportion of approximately 64 gallons.

6. The composition of claim 1 having the copper sulfate present at between about 1.8 and 3.2 pounds per gallon of the water; the citric acid is present at between about 1.18 and 2.57 pounds per gallon of the water; the ammonium carbonate is present at about 0.25 pounds per gallon of the water; the propionic acid is present at between about 0.488 and 0.767 pounds per gallon of the water; the *Yucca schidigera* is present at between about 0.028 and 0.056 gallons per gallon of the water; and the cranberry water is present at between about 0.044 and 0.133 gallons per gallon of the water.

7. The composition of claim 6 comprising having the copper sulfate present at about 2.5 pounds per gallon of the water; the citric acid is present at about 1.88 pounds per gallon of the water; the ammonium carbonate is present at about 0.25 pounds per gallon of the water; the propionic acid is present at about 0.628 pounds per gallon of the water; the *Yucca schidigera* is present at about 0.04 gallons per gallon of the water; and the cranberry water is present at about 0.089 gallons per gallon of the water.

8. A composition for improving the quality and quantity of production in poultry by reducing the incidence of necrotic enteritis, the composition comprising:
    a. sodium acid sulfate;
    b. citric acid; and
    c. cranberry water.

9. The composition of claim 8, having proportions comprising a range of the sodium acid sulfate of between approximately 100 to 400 pounds, and a range of the citric acid of between approximately 100 to 400 pounds both to approximately 1000 gallons of the cranberry water.

10. The composition of claim 9, wherein the sodium acid sulfate is present at a proportion of approximately 0.25 pounds per gallon of the cranberry water and the citric acid is present at a proportion of 0.25 pounds per gallon of the cranberry water.

11. The composition of claim 8, wherein the sodium acid sulfate is present at a proportion of approximately 250 pounds and the citric acid is present at a proportion of approximately 250 pounds to approximately 1000 gallons of the cranberry water.

* * * * *